United States Patent
Lord et al.

(10) Patent No.: US 10,242,156 B2
(45) Date of Patent: Mar. 26, 2019

(54) VISUALIZATION OF CONCURRENTLY EXECUTING COMPUTER INTERPRETABLE GUIDELINES

(75) Inventors: William Palmer Lord, Fishkill, NY (US); Cornelis Conradus Adrianus Maria Van Zon, Fishkill, NY (US)

(73) Assignee: Koninklijke Philips N.A., Eindhoven (NL)

(*) Notice: Subject to any disclaimer, the term of this patent is extended or adjusted under 35 U.S.C. 154(b) by 776 days.

(21) Appl. No.: 13/814,508

(22) PCT Filed: Aug. 16, 2011

(86) PCT No.: PCT/IB2011/053621
§ 371 (c)(1),
(2), (4) Date: Feb. 6, 2013

(87) PCT Pub. No.: WO2012/023104
PCT Pub. Date: Feb. 23, 2012

(65) Prior Publication Data
US 2013/0174084 A1 Jul. 4, 2013

Related U.S. Application Data

(60) Provisional application No. 61/374,786, filed on Aug. 18, 2010.

(51) Int. Cl.
*G06F 19/00* (2018.01)
*G16H 50/20* (2018.01)

(52) U.S. Cl.
CPC ............ *G06F 19/30* (2013.01); *G06F 19/00* (2013.01); *G06F 19/325* (2013.01); *G16H 50/20* (2018.01)

(58) Field of Classification Search
CPC ............ G06F 9/4443; G06F 17/30734; G06F 19/321; G06F 19/322; G06F 19/30; G06F 19/325; G06F 19/345; G06Q 50/24
(Continued)

(56) References Cited

U.S. PATENT DOCUMENTS

| 5,826,237 A | 10/1998 | MacRae et al. |
| 7,988,850 B2 | 8/2011 | Roncadi et al. |

(Continued)

FOREIGN PATENT DOCUMENTS

| WO | 2009003242 A1 | 1/2009 |
| WO | 2010052612 A1 | 5/2010 |

OTHER PUBLICATIONS

Goldstein et al, "Implementing Clinical Practice Guidelines While Taking Account of Changing Evidence: Athena DSS, An Easily Modifiable Decision-Support System for Managing Hypertension in Primary Care", AMIA, 1067, 2000, pp. 300-304.
(Continued)

*Primary Examiner* — Jennifer N To
*Assistant Examiner* — Terri L Filosi

(57) ABSTRACT

A method for visualizing concurrently executing clinical guidelines executed by a clinical decision support system for a subject includes presenting, on a display, a first guideline window in a graphical user interface, wherein the first guideline window presents information corresponding to a first of the concurrently executing clinical guidelines, and presenting, on the display and concurrently with the first guideline window, a second guideline window in the graphical user interface, wherein the second guideline window presents information corresponding to a second of the concurrently executing clinical guidelines.

17 Claims, 4 Drawing Sheets

(58) Field of Classification Search
USPC .............................................. 715/781; 705/3
See application file for complete search history.

(56) References Cited

U.S. PATENT DOCUMENTS

| | | | |
|---|---|---|---|
| 2007/0094188 A1* | 4/2007 | Pandya | G06F 19/345 706/45 |
| 2008/0312961 A1 | 12/2008 | Alsafadi | |
| 2009/0222286 A1* | 9/2009 | Elsholz | G06F 19/322 705/3 |
| 2010/0083164 A1* | 4/2010 | Martin et al. | 715/781 |
| 2010/0131482 A1* | 5/2010 | Linthicum | G06F 19/3406 707/706 |
| 2011/0046979 A1* | 2/2011 | Tulipano | G06F 19/325 705/2 |
| 2011/0208540 A1 | 8/2011 | Lord et al. | |
| 2011/0210853 A1 | 9/2011 | Lord et al. | |
| 2013/0174084 A1 | 7/2013 | Lord et al. | |

OTHER PUBLICATIONS

Dawes, "Co-Morbidity: We Need a Guideline for Each Patient Not a Guideline for Each Disease", Family Practice, 2010, pp. 1-2.
Van Week et al, "Comorbidity and Guidelines: Conflicting Interests", Lancet, 2005, 367(9510), pp. 1-3.

* cited by examiner

VISUALIZATION OF CONCURRENTLY EXECUTING COMPUTER INTERPRETABLE GUIDELINES

The following generally relates to medical informatics and more particularly to visualization of concurrently executing computer interpretable guidelines such as clinical guidelines in connection with a clinical decision support (CDS) system.

A clinical decision support (CDS) system generally is a computing system that facilitates decision-making in the clinical setting. Modern day CDS systems have included interactive software-based systems that assist clinicians with clinical decisions. This has included presenting an interactive graphical user interface (GUI) that a clinician can interact with to help determine diagnosis, analysis, treatment, etc. of patient data. With a CDS system, the clinician provides input, selects analysis options, etc., and the CDS system processes data and presents suggestions and/or analysis results. The clinician reviews the information and ultimately determines what is useful and makes clinical decisions. CDS systems have been used pre-diagnoses, during diagnoses, and post diagnoses (including treatment planning).

CDS systems have been based on computer interpretable guidelines (CIGs). In the healthcare environment, the CIGs have included clinical guidelines. Generally, a clinical guideline is a documented set of recommendations/suggestions for healthcare professionals on how to optimally treat and manage patients with specific diseases and conditions. The recommendations/suggestions are not intended to be rigid rules, but rather pieces of information (e.g., decision options and expected outcomes) to guide clinicians or other authorized users. Guidelines exist for prevention, diagnosis, prognosis, therapy, etc. Sources of clinical guidelines include national or international medical associations or governmental bodies, such as the US Agency for Healthcare Research and Quality, the American Heart Association, etc., as well as local healthcare providers.

Conventionally, clinical guidelines have been sequentially executed, independent of each other, by CDS systems, for each morbidity of interest. Unfortunately, a patient may have a co-morbidity, and such CDS systems are not well-suited for such situations.

Aspects of the present application address the above-referenced matters, and others.

According to one aspect, a method for visualizing concurrently executing clinical guidelines executed by a clinical decision support system for a subject includes presenting, on a display, a first guideline window in a graphical user interface, wherein the first guideline window presents information corresponding to a first of the concurrently executing clinical guidelines, and presenting, on the display and concurrently with the first guideline window, a second guideline window in the graphical user interface, wherein the second guideline window presents information corresponding to a second of the concurrently executing clinical guidelines.

According to another aspect, a system includes a display for displaying information, a storage medium for storing computer executable instructions, and a knowledge base including at least one guideline. The system further includes a processor that executes at least one computer executable instruction in the storage medium and, in response, concurrently presents a graphical user interface via the display, including multiple guideline windows. Each guideline window corresponds to a different guideline of the knowledge base that is concurrently executed by the processor.

According to another aspect, a computer readable storage medium encoded with instructions which, when executed by a processor of a computer, cause the processor to: concurrently present multiple guideline windows, each guideline window corresponding to a different concurrently executing clinical guideline.

The invention may take form in various components and arrangements of components, and in various steps and arrangements of steps. The drawings are only for purposes of illustrating the preferred embodiments and are not to be construed as limiting the invention.

FIG. 1 illustrates an example computing system 100 such as a workstation, a computer, or the like.

Figure 1:
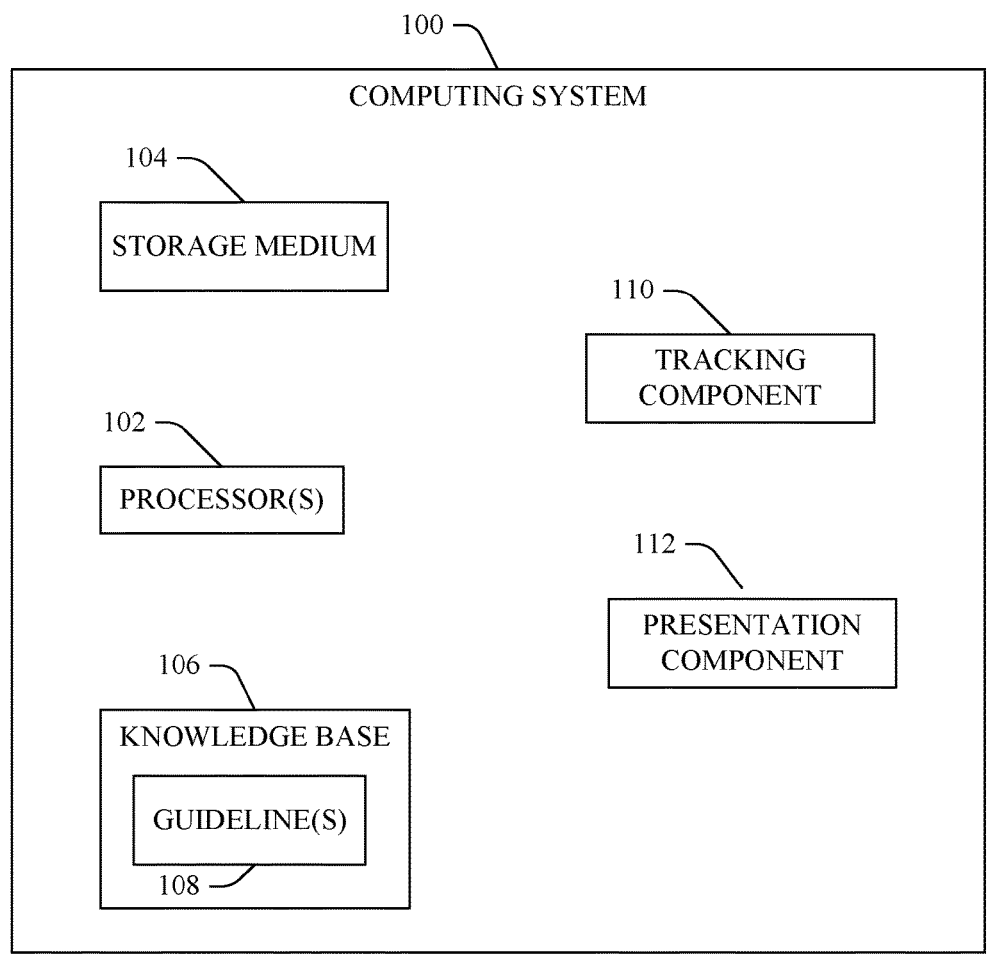
FIG. 1 illustrates an example system configured to concurrently execute multiple clinical guidelines and present information about the concurrently executing multiple clinical guidelines.

The computing system 100 includes one or more processor(s) 102 and computer readable storage medium 104 encoded with computer readable instructions, which, when executed by the one or more processors 102 cause the system 100 to execute decision support (CDS) for a clinician such as a guideline driven or based CDS, which can execute clinical guidelines.

Generally, a clinical guideline is a documented set of recommendations for healthcare professionals on how to optimally treat and manage patients with specific diseases and/or conditions. Suitable guidelines are directed towards, but are not limited to, trauma, myocardial infarction, coronary heart failure, chest pain, asthma, atrial fibrillation, burns, diabetes, drug overdose, earache, gastrointestinal, and/or other clinical guidelines. Guidelines may be specific to a single subject and/or apply to a group of subjects.

A knowledge base 106 includes one or more guidelines 108 such as at least one clinical guideline that can be executed by the CDS system. The knowledge base 106 can be local (as shown), remote from the system 100, part local and part remote, distributed, and/or otherwise configured in a known manner.

The illustrated system 100 is configured to execute guidelines both one at a time or concurrently. An example of a system that focuses on executing one guideline at a time is described in PCT/IB2009/054775, filed on Nov. 6, 2008, and entitled "Executable Clinical Guideline and Guideline Tool," which is incorporated herein by reference in its entirety. An example of a system that can concurrently execute multiple guidelines is described in PCT/IB2009/054779, filed on Nov. 6, 2008, and entitled "Method and System for Simultaneous Guideline Execution," which is incorporated herein by reference in its entirety.

A tracking component 110 facilitates tracking performance of executing guidelines, including individual guidelines and concurrently executing guidelines. The tracking component 110 is implemented through hardware and/or software. By way of example, the tracking component 110 may be implemented through one or more of the processors 102 and/or one more other processors executing instructions in the storage medium 104 and/or other storage medium.

A presentation component 112 such as a display, a monitor, or the like is employed to visually present information corresponding to the individual guidelines and concurrently executing guidelines, including, but not limited to, information from the tracking component 110 and/or other information. As described in greater detail below, the processor(s) 102 execute computer readable instructions in the storage medium 104 that cause the presentation component 112 to present an interactive graphical user interface (GUI) in which information corresponding to different concurrently executing guidelines is presented in different concurrently presented windows of the GUI.

As utilized herein, a window is a visualization area or region of the interactive GUI that presents (or visually outputs) information and/or accepts input or information. One or more windows can be superimposed over, graphically placed behind, and/or move around (e.g., via mouse or the like) in connection with one or more other windows. Such windows may be independent or dependent upon another window.

Concurrently presenting multiple windows for concurrently executing guidelines facilitates providing clinical support decision recommendations for subjects that may have co-morbidities (more than one disease/condition at a time) in which each morbidity may correspond to a separate specific guideline. It also allows for running multiple probable diagnostic guidelines in parallel, where the appropriate guideline(s) may not be known until the diagnostic process is complete (e.g., a differential diagnosis), until one or more proves out. Moreover, care providers may have different roles and can require/prefer role specific guidelines and/or views on the guidelines, and concurrently presenting multiple windows for concurrently executing guidelines allows for running the different guidelines simultaneously.

It is to be appreciated that the system 100 may be a standalone computing system or part of a network distributed across multiple healthcare provision sites.

Figure 2:
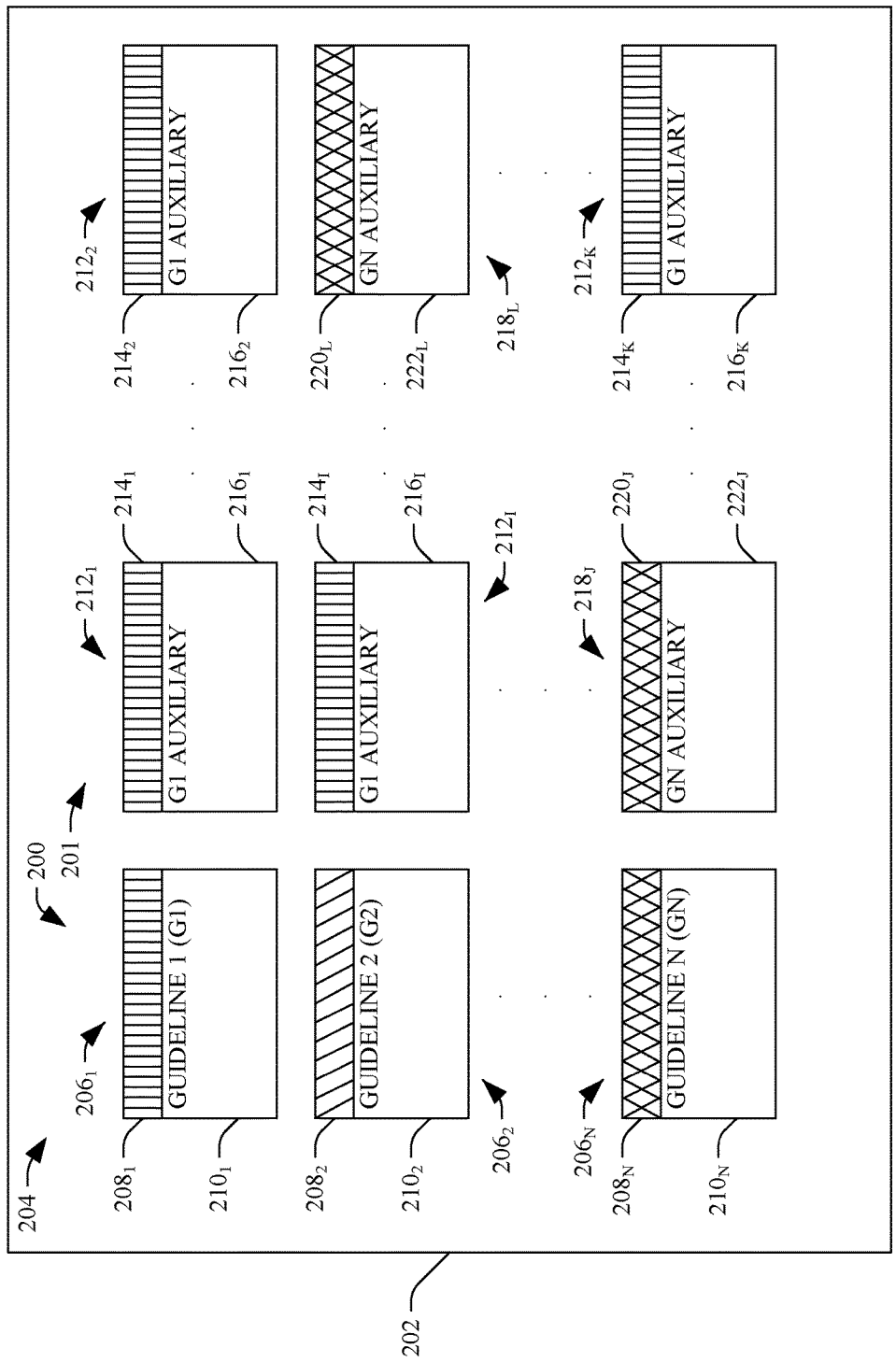
FIG. 2 illustrates an example graphical user interface (GUI) that presents information corresponding to the concurrently execute multiple clinical guidelines.

FIG. 2 illustrates an example graphical user interface (GUI) 202 that presents information corresponding to the concurrently execute multiple clinical guidelines. The illustrated GUI 202 includes a plurality (N×M) of widows 204 (where N and M are integers equal to or greater then one), including guideline windows 200 and guideline auxiliary (form) windows 201.

The guideline windows 200 include a first window $206_1$ that corresponds to a first executing clinical guideline. The first window $206_1$ includes a first information region $210_1$ for presenting information about the first executing guideline. For example, such information includes as a flow diagram or chart of the tasks and/or decisions and/or other information of the first executing guideline.

The first window $206_1$ also includes a first identification region $208_1$, which includes a first unique identifier for the first executing clinical guideline. In this example, the first unique identifier includes a first unique pattern (i.e., vertical lines). Additional or alternative unique identifiers, such as, but not limited to, a color, a shape, name of guideline, symbol representing the guideline, etc., can be used.

The guideline windows 200 further include a second window $206_2$ that corresponds to a second executing clinical guideline and includes a second identification region $208_2$, which includes a second unique identifier for the second executing clinical guideline. The second unique identifier includes a second unique pattern (i.e., diagonal lines), which is different from the first unique identifier. The second window $206_2$ also includes a second information region $210_2$ for presenting information about the second executing guideline.

An Nth window $206_N$ corresponds to an Nth executing clinical guideline and includes an Nth identification region $208_N$, which includes an Nth unique identifier for the Nth executing clinical guideline. The Nth unique identifier includes an Nth unique pattern (i.e., cross-hatch), which is different from the first and second unique identifiers. The Nth window $206_N$ further includes an Nth information region $210_N$ for presenting information about the Nth executing guideline.

The first, second and Nth unique identifiers facilitate distinguishing concurrently presented guideline windows based on an executing guideline.

The guideline auxiliary windows 201 include a first auxiliary window $212_1$ corresponding to the first window $206_1$ and hence the first executing clinical guideline. The first auxiliary window $212_1$ includes first information region $216_1$ for presenting the information. In this embodiment, the first information region $216_1$ presents further information for a flow block presented in the flow diagram in the first window $206_1$. The first auxiliary window $212_1$ also includes an identification region $214_1$ populated with the first unique identifier, which provides a visual link between the auxiliary window $212_1$ and the first window $206_1$.

Likewise, second, Ith, and Kth auxiliary windows $212_2$, $212_1$, and $212_K$ correspond to the first window $206_1$ and hence the first executing clinical guideline. The first auxiliary windows $212_2$, $212_1$, and $212_K$ also include information regions $216_2$, $216_1$, and $216_K$ for presenting the information, such as information corresponding to other flow blocks of the flow diagram in the first window $206_1$ and/or other information. The auxiliary windows $212_2$, $212_1$, and $212_K$ further include identification regions $214_2$, $214_1$, and $214_K$ populated with the first unique identifier, which provides a visual link between the auxiliary window $212_2$, $212_1$, and $212_K$ and the first window $206_1$.

In the illustrated embodiment, there are no visible auxiliary windows 201 for the second executing guideline and corresponding second window $206_2$. However, in other embodiments, auxiliary windows 201 may be visible in the GUI 202 for the second executing guideline and corresponding second window $206_2$.

The guideline auxiliary windows 201 further include a Jth auxiliary window $218_J$ corresponding to the Nth window $206_N$ and hence the Nth executing clinical guideline. Similarly, the Jth auxiliary window $218_J$ presents further information (for a flow block presented in the flow diagram in the Nth window $206_N$) in an information region $222_J$ and has an identification region $220_J$ that includes the Nth unique identifier of the Nth guideline window $206_N$.

The guideline auxiliary windows 201 also include a Lth auxiliary window $218_L$ corresponding to the Nth window $206_N$ and hence the Nth executing clinical guideline. Likewise, the first auxiliary window $218_L$ presents further information (for a flow block presented in the flow diagram in the Nth window $206_N$) in an information region $222_L$ and has an identification region $220_L$ that includes the Nth unique identifier of the Nth guideline window $206_N$.

With FIG. 2, it is to be appreciated that the illustrated location of the unique identifier and the information region in a window 204 is not limiting, and other configurations are contemplated herein. In addition, one or more additional regions may be defined within one or more of the windows 204. It is also to be appreciated that one or more of the windows 204 in the GUI 202 may be closed, and additional guideline windows 200 and/or auxiliary windows 201 may be opened. A newly opened window will be automatically placed in an open slot. If no open slot is available the GUI 202 will automatically scale down the size of all open windows to create a slot. Likewise, as a window is closed, the GUI 202 will automatically scale up all remaining windows to maximize the use of available space.

Furthermore the location and/or geometry (e.g., size, shape, etc.) of the windows 204 can be different. For example, the user can selectively drag and drop and/or modify the geometry of the windows 204 within the GUI 202. Moreover, virtual GUI space can be created where the windows 204 exceed the viewable region of the GUI. In this instance, an interactive scroll bar or the like can be presented to allow a user to move windows 204 in and out of the viewable region of the GUI 202.

Figure 3:
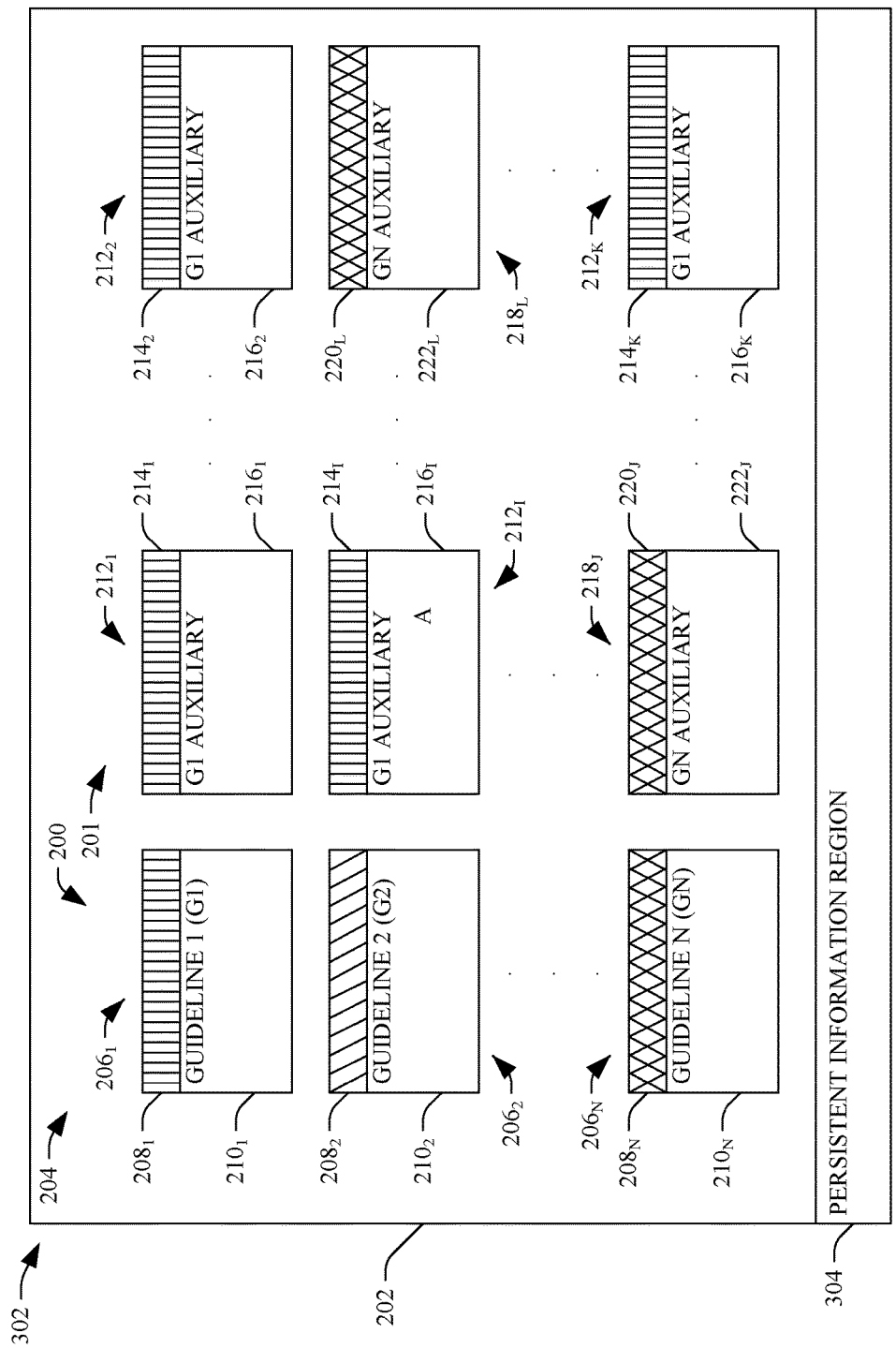
FIG. 3 illustrates an example user interface (GUI) that presents information corresponding to the concurrently execute multiple clinical guidelines and a persistent information window.

FIG. 3 illustrates an example GUI 302, which includes the GUI 202 and a persistent information window 304. The persistent data window 304 is used to present data, alerts, timers, to do items, and/or other information so that they are always available, independent of context and/or subject. The information populated in the persistent information window 304 includes for example information specified in default and/or user preferences, and/or information (e.g., a task parameter) manually moved to the persistent information window 304 by a user via drag and drop and/or other interaction between the GUI 302 and the user.

In the illustrated embodiment, the persistent information window 304 is located below the GUI 202. Alternatively, the persistent information window 304 may be otherwise positioned, for example, on top of the GUI 202, to a side of the GUI 202, and/or otherwise. Moreover, the persistent information window 304 may be manually re-located by a user of the system 100, for example, by dragging and dropping the GUI 202. The persistent information window 304 may also be closed by the user and the geometry thereof may be changed by the user.

Figure 4:
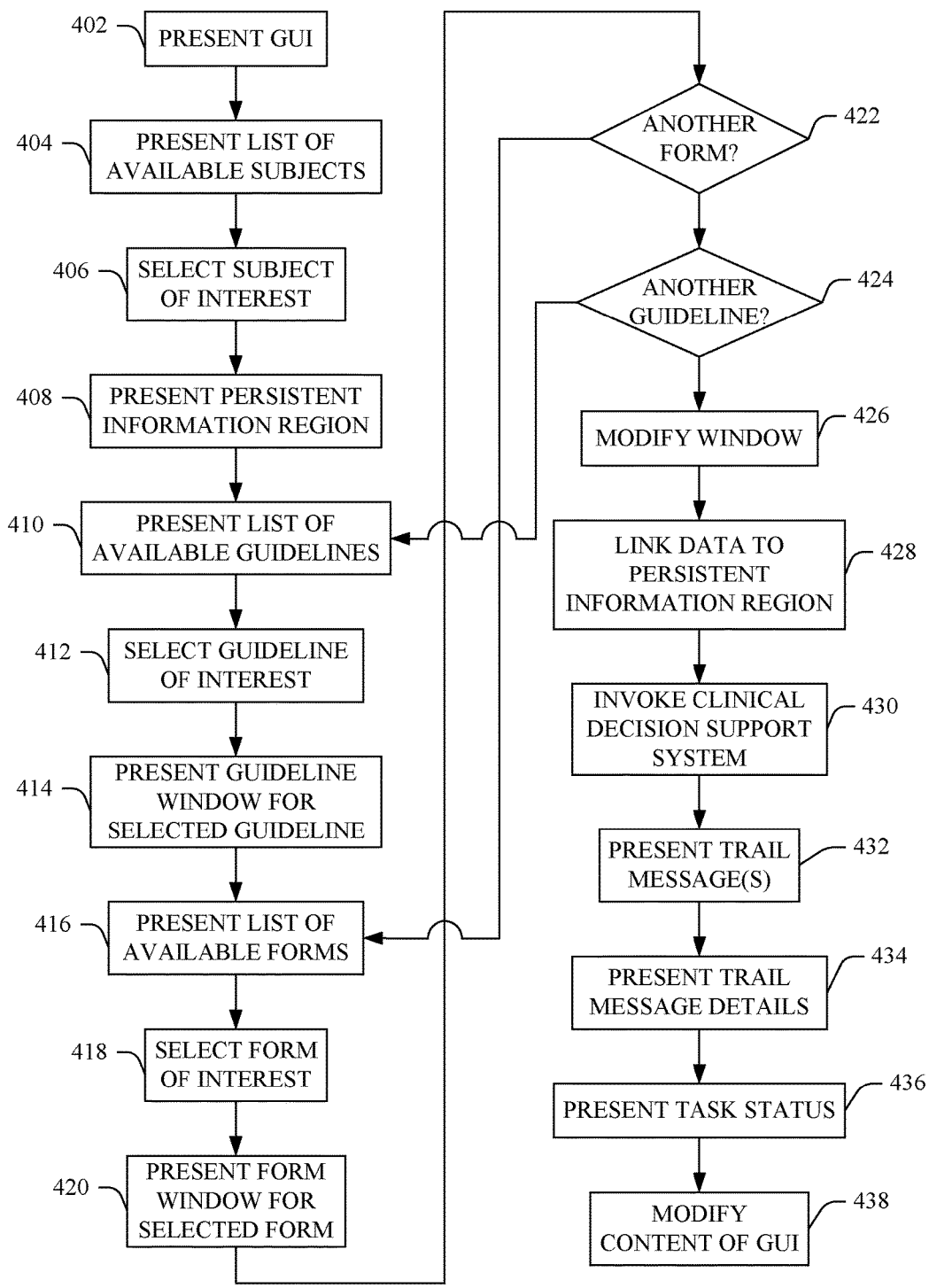
FIG. 4 illustrates an example method for visualizing information about concurrently executing clinical guidelines.

FIG. 4 illustrates an example workflow diagram for concurrently visualizing simultaneously or concurrently executing computer interpretable guidelines.

It is to be appreciated that the ordering of the following acts is not limiting. As such, other orderings are contemplated herein. In addition, one or more acts may be omitted and/or one or more additional acts may be included.

At 402, a system (e.g., the system 100) configured to execute and track clinical guidelines, presents an interactive graphical user interface (GUI). The GUI is rendered based on default or user preferences, which includes one or more guidelines.

At 404, a select subject menu of the GUI presents a list of available subjects.

At 406, a user of the system selects a subject of interest from the list of subjects.

At 408, a persistent information window of the GUI is populated with information, as described herein.

At 410, a select guideline menu of the GUI provides a list of available guidelines.

At 412, the user of the system selects a first guideline of interest from the list of available guidelines.

At 414, a guideline window, which includes a unique characteristic corresponding to the selected guideline and an information region, is presented in connection with the GUI. As described herein, the unique characteristic includes a unique color, pattern, symbol, name, or the like.

At 416, a select form menu of the GUI provides a list of available forms for guidelines.

At 418, the user of the system selects a form of interest from the list of available forms.

At 420, a form window, which includes the unique characteristic corresponding to the selected guideline and an information region, is presented in the GUI. The form window is linked to the corresponding guideline and presents information corresponding thereto, for example, to a flow block of a flow diagram of the guideline window.

At 422, acts 416 and 420 are repeated for one or more forms of interest, wherein a different form window is presented for each selected form. Note that an opened form window can be closed. In addition, a form window can be opened for a guideline that has not been opened yet. In this instance, the form window can be contextually linked to the guideline, and a guideline window may automatically be opened for the form.

At 424, acts 410-422 are repeated for one or more guidelines interest, wherein the guideline windows for each selected guideline are concurrently presented in the GUI, and a different unique characteristic is used for each guideline and associated forms. Note that an opened guideline window can be closed.

FIGS. 2 and 3 illustrate examples GUI 202 and 302 with guideline windows 200 and corresponding auxiliary (form) windows 201 for concurrently executing guidelines.

At 426, one or more of the guideline windows and/or the form windows is adjusted within the GUI. This can be done during and/or after creation of each window. In one instance, this includes selectively positioning or moving a window within the GUI, for example, by dragging and dropping a window. Additionally or alternatively, this includes re-sizing a window, for example, by clicking and dragging on a corner or side of a window, zooming in and out, etc.

At 428, information from one or more of the presented windows is manually included and/or linked to the persistent information window, for example via dragging and dropping the one or more fields in the information window.

At 430, a decision support menu of the GUI is used to invoke a decision support system.

At 432, an audit window of the GUI presents trail messages for executing guidelines.

At 434, a pop-out window is presented, if a message in the audit window is selected, with information corresponding to the selected message.

At 436, a "to-do" window is invoked to show a status of the tasks for each guideline, including partially finished tasks, recommended next tasks, current tasks from among all currently active guidelines, and/or other information. The unique characteristic is shown along with each guideline. The "to-do" window can be used to present such data in one or more windows without showing the sequence of events (i.e., the collection of graphical guideline representations in the other windows) to get to the displayed information.

At 438, one or more guideline and/or form windows can be closed and/or opened, the particular subject can be changed, and/or the GUI can be otherwise modified and/or closed.

Various approaches can be used to identify conflicts and/or redundancy amongst concurrently executing guidelines and/or presenting a notification indicating the conflict and/or redundancy. A non-limiting example of a conflict follows. One guideline might recommend rapid intravenous infusion of fluids (to increase blood pressure due to blood loss) whereas a concurrently executing guideline might recommend a diuretic (to lower blood pressure and reduce the strain on the heart).

Non-limiting examples of redundancies follow. Two concurrently executing guidelines might recommend a chest x-ray. In another example, one guideline may recommend infusing two (2) liters of Ringers Lactate and another guideline may recommend infusing two (2) liters of D5W, where these two different orders address the same underlying treatment goal.

One approach for identifying conflicts and/or redundancy includes providing a design time tool to directly express/specify goals of variables (data), orders, treatments, diagnostic tools, etc. These could then be compared at run-time.

Another approach includes employing a run-time inference engine and incorporating ontologies to infer relationships and purposes of variables (data), orders, treatments, diagnostic tools, etc. By way of example, with the above example where one guideline recommends increasing vasculature volume and a concurrently executing guideline recommend decreasing vasculature volume, the inference engine can conclude that increasing vasculature volume and decreasing vasculature volume are in direct conflict. The inference engine can notify a user of the system and/or the system about the conflict.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

What is claimed is:

1. A method for visualizing concurrently executing clinical guidelines for a same subject executed by a decision support system, comprising:
   presenting, on a display, a first guideline window in a graphical user interface, wherein the first guideline window presents information corresponding to a first of the concurrently executing clinical guidelines and the first guideline window includes a first unique identifier that represents the first guideline window and the first of the concurrently executing clinical guidelines;
   presenting, on the display and concurrently with the first guideline window, a second guideline window in the graphical user interface, wherein the second guideline window presents information corresponding to a second of the concurrently executing clinical guidelines, and the second guideline window includes a second unique identifier that represents the second guideline window and the second of the concurrently executing clinical guidelines; and
   presenting, on the display, for at least one of the guideline windows, one or more auxiliary windows that presents further information corresponding to the concurrently executing clinical guideline of the at least one of the first guideline window and the second guideline window, and the one or more auxiliary windows includes an identifier corresponding to at least one of the first or second unique identifiers, wherein each of the concurrently executing clinical guidelines for the same subject includes a documented set of recommendations to treat and manage a different morbidity of the same subject;
   wherein a clinical guideline is a documented set of recommendations to treat and manage a morbidity;
   wherein an executing clinical guideline includes a clinical guideline retrieved and displayed in response to an input indicative of a condition or disease of the subject which corresponds to the morbidity of the clinical guideline, and the executing clinical guideline includes a modification of received and displayed clinical guidelines in response to an input indicating at least one recommendation of the documented set of recommendations is completed, wherein each concurrently executing clinical guideline comprises a different executing clinical guideline for the same subject;
   monitoring data related to each concurrently executing clinical guideline;
   determining whether a first set of the documented sets of recommendations of one of concurrently executing clinical guidelines is to be displayed based on the monitored data;
   identifying at least one of a conflict or redundancy between the documented sets of recommendations of the concurrently executing clinical guidelines using an ontology; and
   providing a notification indicative of the conflict or redundancy.

2. The method of claim 1, further comprising:
   presenting, on the display and concurrently with at least one of the first or second guideline windows, one or more other guideline windows in the graphical user interface, wherein the one or more other guideline windows respectively presents information corresponding to one or more of the concurrently executing clinical guidelines.

3. The method of claim 1, wherein the identifier includes one or more of a color, a pattern, or a symbol unique to the first or second concurrently executing clinical guideline.

4. The method of claim 1, wherein the further information corresponds to a task in a flow diagram presented in the at least one of the first and second guideline windows.

5. The method of claim 1, further comprising: presenting, in connection with each auxiliary window, the unique identifier of the corresponding guideline window.

6. The method of claim 1, further comprising:
   presenting, on the display, a persistent information region presenting at least one of data, an alert, a timer, a to do item, or user-selected parameter.

7. The method of claim 6, wherein the information presented in the persistent information region is always visible in the GUI.

8. The method of claim 6, wherein the information presented in the persistent information region alternatively corresponds to the subject associated with the concurrently executing clinical guidelines or a different subject.

9. The method of claim 1, wherein at least one of the conflict or redundancy between two or more concurrently executing clinical guidelines is identified based on a comparison of at least one of a goal, an order, a treatment, or a diagnostic tool of the two or more concurrently executing clinical guidelines.

10. The method of claim 1, wherein at least one of the conflict or redundancy is identified of two or more concurrently executing clinical guidelines by inferring based on the ontology at least one of relationship or purpose of at least one of a goal, an order, a treatment, or a diagnostic tool of the two or more concurrently executing clinical guidelines.

11. The method of claim 1, further comprising:
   presenting, on the display, a to do window that presents at least one of a status of a task for one or more executing clinical guidelines, a recommended next task, or a current task from among active concurrently executing clinical guidelines, in a single window without showing a sequence of a clinical guideline to get items in the to do window.

12. A system, comprising:
a display for displaying information;
a storage medium for storing computer executable instructions;
a knowledge base including a plurality of executable clinical guidelines; and
a processor that executes at least one computer executable instruction in the storage medium and, in response, concurrently presents a graphical user interface via the display, including windows of a plurality of executing guidelines from the knowledge base, wherein each window of the plurality of executing guidelines corresponds to a different clinical guideline of the knowledge base that is concurrently executed by the processor and each window of the plurality of executing guidelines includes a unique identifier, and at least one of the of the plurality of executing guidelines includes one or more auxiliary windows that presents further information corresponding to one window of the windows of the plurality of executing guidelines, and the one or more auxiliary windows includes an identifier corresponding to the unique identifier of the one window of the windows of the plurality of executing guidelines, wherein each of the windows of the plurality of executing guidelines include a documented set of recommendations to treat and manage a different morbidity of a same subject;
wherein a clinical guideline is a documented set of recommendations to treat and manage a morbidity;
wherein an executing clinical guideline includes a clinical guideline retrieved and displayed in response to an input indicative of a condition or disease of the subject which corresponds to the morbidity of the clinical guideline, and the executing clinical guideline includes a modification of received and displayed clinical guideline in response to an input indicating at least one recommendation of the documented set of recommendations is completed, wherein each concurrently executing clinical guideline comprises a different executing clinical guideline for the same subject;
wherein each window of the plurality of executing clinical guidelines is a separate and distinct window, and the processor identifies using an ontology at least one of a conflict or a redundancy between at least two different guidelines of the plurality of executing clinical guidelines concurrently executed by the processor.

13. The system of claim 12, wherein the processor presents a list of available subjects in a select subject menu, receives a subject select signal indicative of a user selected one of the subjects from the list of available subjects in the select subject menu, and populates a persistent information window of the graphical user interface with information based thereon.

14. The system of claim 13, wherein the processor presents a list of available executable clinical guidelines in a select guideline menu, receives a guideline select signal indicative of a user selected one of the guidelines from the list of available executable clinical guidelines in the select guideline menu, and displays one of the windows of the plurality of executing guidelines in response thereto, wherein the one window of the windows of the plurality of executing guidelines includes the unique identifier corresponding to the selected guideline.

15. The system of claim 14, wherein the processor presents a list of available form for guidelines in a select form menu, receives a form select signal indicative of a user selected one of the form from the list of available forms in the select form menu, and displays a form windows, which includes the unique identifier.

16. The system of claim 15, wherein the form window is linked to corresponding guideline and presents a flow block of a flow diagram of the one window of the windows of the plurality of executing guidelines.

17. The system of claim 12, wherein the unique identifier includes one or more of a color or a pattern of a window identifier unique to one of the windows of the plurality of executing guidelines.

* * * * *